United States Patent
Wada et al.

Patent Number: 5,890,898
Date of Patent: Apr. 6, 1999

[54] INFECTION CONTROL GUARD FOR DENTAL AIR-WATER SYRINGES

[76] Inventors: Eric Minoru Wada, 764 W. Lancaster Blvd., Lancaster, Calif. 93534; Bridget Karen Samp, 40018 Castana La.; Jennifer Ann Park, 40540 Via Verdad, both of Palmdale, Calif. 93551

[21] Appl. No.: 929,309

[22] Filed: Sep. 3, 1997

Related U.S. Application Data

[63] Continuation-in-part of Ser. No. 622,580, Mar. 25, 1996, which is a continuation-in-part of Ser. No. 319,665, Oct. 7, 1994, abandoned, which is a continuation of Ser. No. 103,211, Nov. 8, 1993, abandoned.

[51] Int. Cl.$^6$ .................................................. A61C 1/16
[52] U.S. Cl. .......................................................... 433/116
[58] Field of Search ............................. 433/80, 116, 114

[56] References Cited

U.S. PATENT DOCUMENTS

| | | |
|---|---|---|
| 362,808 | 5/1887 | Wood . |
| 4,281,986 | 8/1981 | Erickson . |
| 4,386,911 | 6/1983 | Maloney .................................. 433/125 |
| 4,424,036 | 1/1984 | Lokken .................................... 433/116 |
| 4,600,387 | 7/1986 | Ross . |
| 4,611,992 | 9/1986 | Lokken . |
| 4,820,155 | 4/1989 | Sauveur . |
| 4,828,491 | 5/1989 | Gray . |
| 4,850,868 | 7/1989 | Wright et al. . |
| 5,067,899 | 11/1991 | Paschal .................................... 433/80 |
| 5,197,876 | 3/1993 | Coston . |
| 5,275,559 | 1/1994 | Rihel ....................................... 433/116 |
| 5,376,003 | 12/1994 | Rizkalla .................................. 433/116 |
| 5,547,376 | 8/1996 | Harpel ..................................... 433/116 |

FOREIGN PATENT DOCUMENTS

| | | | |
|---|---|---|---|
| 492732 | 5/1953 | Canada .................................... 433/80 |
| 4029369 | 3/1992 | Germany ................................. 433/80 |

*Primary Examiner*—Ralph A. Lewis

[57] ABSTRACT

A multifunctional splash guard for a dental air-water syringe comprising of a cone shaped member having a generally cylindrical base formed with an axial opening extending through said base formed to permit insertion of the tip of a dental air-water syringe through said opening to allow positioning of said tip within said cone shaped member and with its soft flexible plastic-like material one piece make up, allowing for not only controlling and containing back-spray, but also increasing the effectiveness of all rinsing and drying procedures and aids in tongue and cheek retraction.

6 Claims, 2 Drawing Sheets

INFECTION CONTROL GUARD FOR DENTAL AIR-WATER SYRINGES

RELATED CASES

This application is a continuation-in-part of patent application Ser. No. 08/622,580, Filed Mar. 25, 1996 currently pending, which is a continuation-in-part of patent application Ser. No. 08/319,665, Filed Oct. 7, 1994 abandoned, which is a continuation of patent application Ser. No. 08/103,211, Filed Nov. 8, 1993 abandoned.

FIELD OF INVENTION

This invention relates to dental equipment and is especially directed to splash guards for dental air-water syringes to prevent contamination of persons and articles nearby.

PRIOR ART

It is common practice for dentists and their staff to use air-water syringes to clean and rinse a patients mouth to remove saliva, blood and dental materials in the vicinity in which they are working and to assist in drying dental materials. Unfortunately, the use of such air/water syringes often causes blood, saliva and other bacteria laden material to be splattered out of the patients' mouth and to contaminate persons and articles nearby. This can lead to transfer of infection, which can be serious or even fatal. Numerous prior art devices have been proposed for accomplishing this purpose. However, many of the prior art devices have been complex, bulky and difficult to use. Also none of the prior art devices enhance and broaden the function of the air-water syringe. A search in the U. S. Patent Office has revealed the following:

| U.S. PAT. NO. | INVENTOR | ISSUED |
|---|---|---|
| 362,808 | WOOD | |
| 4,281,986 | ERICKSON | |
| 4,600,387 | ROSS | |
| 4,611,992 | O. LOKKEN | JAN. 3, 1984 |
| 4,820,155 | SAUVEUR | |
| 4,828,491 | GRAY | |
| 4,850,868 | WRIGHT | |
| 5,197,876 | P. COSTION | MAR. 30, 1993 |
| 5,376,003 | A. RIZKALLA | DEC. 27, 1994 |

Each of these references is subject to the disadvantages discussed above. Thus, none of the prior art dental splash guards have been entirely satisfactory. None of the prior art devices enhance and increase the efficiency of the dental air-water syringe by containing and controlling the air/water and provide tongue and cheek retraction.

BRIEF SUMMARY AND OBJECTS OF INVENTION

These disadvantages of the prior art are overcome with the present invention and improved dental splash guard which is simple in construction, compact in size, easy to install, provides positive protection against undesired back spray, contains and controls air/ water and debris, and increases the effectiveness of all rinsing and drying procedures while aiding in tongue and cheek retraction.

These advantages of the present invention are attained by providing an improved, multifunctional dental splash guard comprising of a cone shaped member having a generally cylindrical base formed with an axial opening extending through said base formed to permit insertion of the tip of a dental air-water syringe through said tip within said cone shaped member.

Accordingly, it is an object of the present invention to provide an improved, multifunctional dental splash guard that enhances and broadens the function of the dental air-water syringe by creating a "washing machine" like effect during rinsing and drying procedures and aid in tongue and cheek retraction.

An additional object of the present invention is to provide improved means for preventing splashing and splattering of blood, saliva and the like by a dental air-water syringe.

A further object of the present is to provide an improved splash guard for a dental air-water syringe that is simple in construction.

Another object of the present invention is to provide an improved splash guard for a dental air-water syringe that increases the effectiveness of the dental air-water syringe by containing and controlling splattering and splashing.

An additional object of the present invention is to provide an improved splash guard for a dental air-water syringe that is compact in size and easy to install.

A further object of the present invention is to provide an improved splash guard for a dental air-water syringe which provides more effective utilization of the air-water syringe during rinsing and drying procedures and tongue and cheek retraction.

A specific object of the present invention is to provide an improved splash guard for a dental air-water syringe comprising a conical member having a generally cylindrical base formed with an axial opening extending through said base formed to permit insertion of the tip of a dental air-water syringe through said opening to allow positioning of said tip within said conical member.

These and other objects and features of the present invention will be apparent from the following detailed description, taken with reference to the figures of the accompanying drawing.

DETAILED DESCRIPTION OF THE INVENTION

Figure 1:
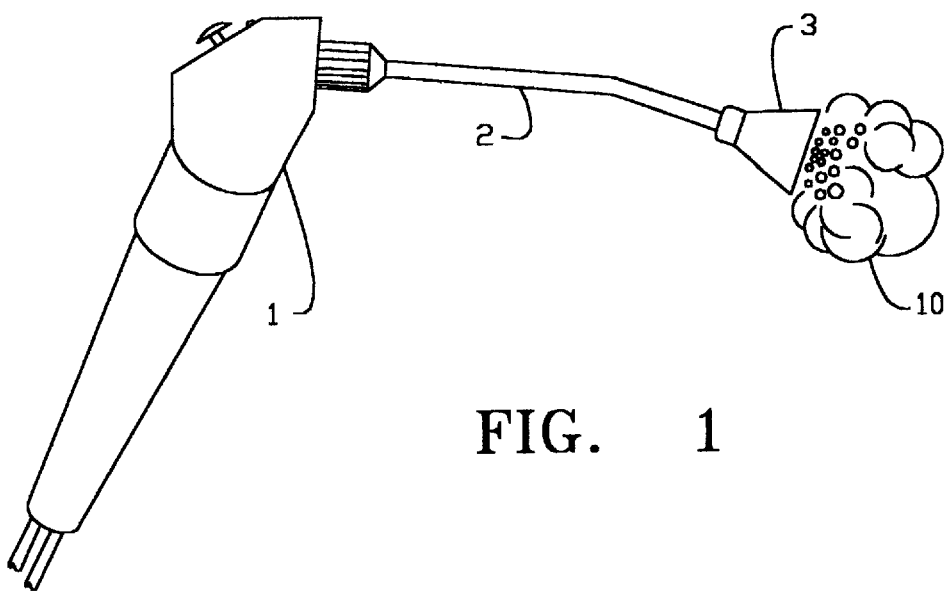
FIG. 1 is an isometric side view showing a dental air-water syringe having a splash guard embodying the present invention.
Figure 2:
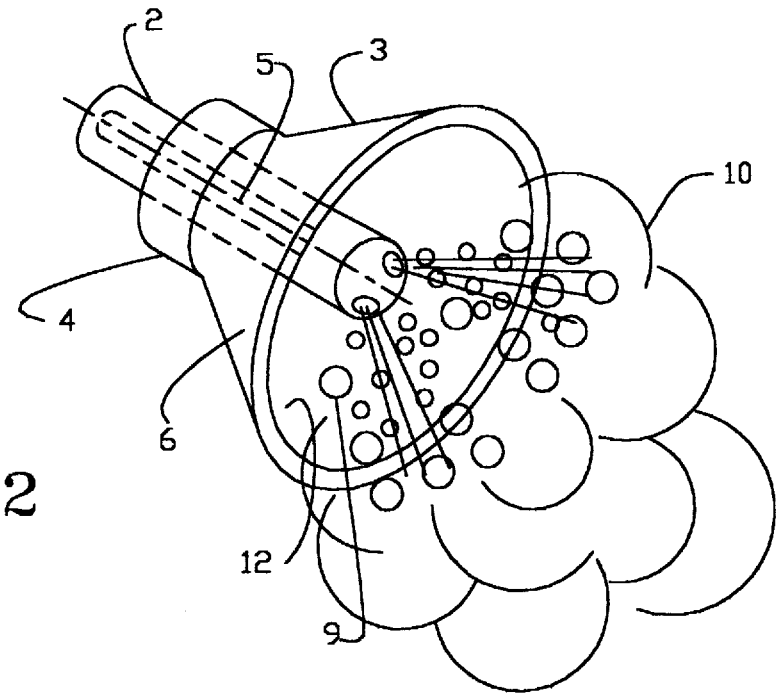
FIG. 2 is an enlarged isometric front view showing the front end of the splash guard of FIG.1.
Figure 3:
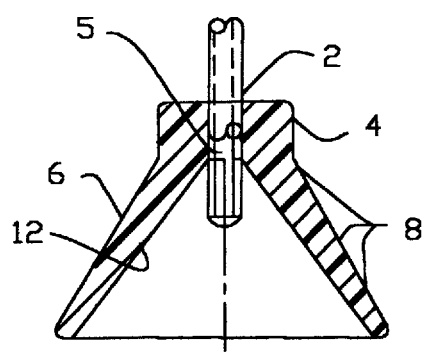
FIG. 3 is a vertical section through the splash guard of FIG. 1.

In that form of the present invention chosen for purposes of illustration in the drawing, FIG. 1 shows a dental air-water syringe 1 having a tip 2 on which is mounted a splash guard 3, embodying the present invention, shown during irrigation of a work site, indicated generally at 10. As best seen in FIGS. 2 and 3, the splash guard 3 has a generally cylindrical sleeve 4, formed with an opening 5 extending axially through the sleeve 4 to releasable receive and frictionally grip the tip 2 of the dental air-water syringe 1. Forward of the sleeve 4, the splash guard 3 has a skirt 8 which flares outwardly in a generally cone shaped manner, as seen at 8. The outer rim 9 of the skirt 8 is preferably slightly larger than the diameter as a normal tooth 10, while the inner wall 12 of the skirt 8 sloped from the rim 9 to the opening 5.

In use, the dentist or his assistant can slip the tip 2 of the dental air-water syringe 1 through opening 5 in the sleeve 4 until the tip 2 projects beyond the opening 5 adjacent the inner wall 12 of the splash guard 3. Thereafter, the dentist proceeds to use the dental air-water syringe 1 in the usual manner. However, because the splash guard 3 surrounds the tip 2 and is slightly larger than the tooth 10, the splash guard 3 will serve to contain and control splashing and will prevent blood, saliva and debris and the like from being splattered out of the patient's mouth to contaminate clothing, people or other nearby objects. Also, the splash guard 3 will increase the effectiveness of the air-water syringe during all rinsing and drying procedures, and will aid in tongue and cheek retraction. When the dentist completes work on the patient, the splash guard 3 can be removed quickly and easily, by sliding it off of the tip 2 of the dental air-water syringe 1 for discarding.

The applicant's device is intended to work in combination with the air-water syringe.

The nozzle terminal end of the air-water syringe is positioned inside the applicant's splash guard. In this manner, the soft, flexible skirt is held directly on the tooth while the nozzle terminal end of the air-water syringe is held off the tooth.

The space created, along with the cone shape of the applicant's device is what engenders the powerful "washing machine" like effect that enhances all rinsing and drying procedures. By containing and controlling the splashing of blood, saliva and tooth debris, infectious back spray is eliminated.

The applicant's device is preferably made of a relatively clear, soft, flexible material wherein it can accommodate a variety of tooth shapes. Also, by conforming to the surface it is laterally pressed against, the present device can move, hold and retract the soft tissue of the tongue and cheek and do it without causing tissue trauma.

Figure 4:
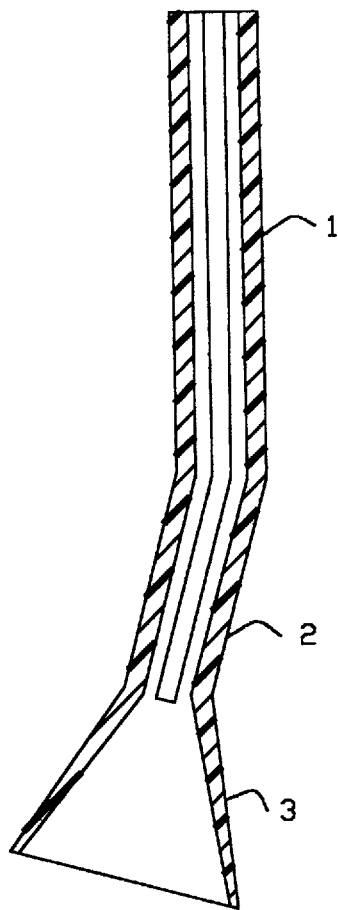
FIG. 4 is a side view showing the dental air-water syringe and applicants splash guard as a one-unit device.

Obviously, numerous variations and modifications can be made without departing from the spirit of the present invention. Therefore, it should be clearly understood that the form of the present invention described above and shown in the figures of the accompanying drawing are illustrative only and are not intended to limit the scope of the present invention. The present invention FIG. 4 can also be made as one (1) unit with the air-water syringe tip.

We claim:

1. A dental device for preventing splattering when spraying a patient's teeth with air and/or liquid from a dental syringe, comprising:

an elongated tubular syringe tip having opposed proximal and distal ends with a flow passage extending therebetween for conveying air and/or liquid from a dental syringe to a patient's teeth, and a splash guard comprising a tubular sleeve having a proximal and a distal end with a relatively constant diameter axial opening extending from the proximal end to the distal end of the sleeve, said tubular syringe tip extending through and being secured in the axial opening of said sleeve, said splash guard further comprising a cone shaped flexible skirt expanding outwardly from a first end connected to said tubular sleeve distal end to a second end, wherein said syringe tip distal end is positioned between said first and second ends of said cone shaped skirt, said flexible skirt further including inner and outer surfaces wherein said inner surface and said outer surface of the flexible skirt are tapered relative to each other from the first end of the skirt to the second end of the skirt, whereby the second end of the skirt is more flexible than the first end to permit the guard to be placed comfortably adjacent the tooth of a patient.

2. The dental device of claim 1, wherein said flexible skirt is transparent.

3. The dental device of claim 1, wherein said flexible skirt extends outwardly from said sleeve at an angle of between 30 to 60 degrees.

4. The dental device of claim 1, wherein the splash guard is comprised of rubber, silicone, or polyvinyl chloride.

5. The dental device of claim 1, wherein the securement between the syringe tip and the splash guard sleeve is a releasable frictional securement.

6. A method of spraying a patient's teeth with air and/or liquid from a dental syringe comprising:

positioning a splash guard, comprised of a tubular sleeve and a cone shaped flexible skirt that expands outwardly from a first end connected to said tubular sleeve to a second end, on a dental syringe tip such that the distal end of the dental syringe tip is between said first and second ends of said flexible skirt and such that the dental syringe tip extends through and contacts a relatively constant diameter axial opening extending from one end of the sleeve to the other, pressing the flexible skirt of said splash guard, which further includes inner and outer surfaces which taper relative to one another, against the patient's teeth so as to conform at least in part to the shape of the tooth pressed against, directing liquid and/or air from the dental syringe through the syringe tip to the patient's teeth, wherein the splash guard directs liquid and/or air back towards the teeth thereby enhancing the rinsing or drying of the dental surfaces and preventing the splattering of the patient and user.

* * * * *